United States Patent [19]
Howard et al.

[11] Patent Number: 5,817,097
[45] Date of Patent: Oct. 6, 1998

[54] BONE SAW BLADE GUIDE WITH MAGNET

[75] Inventors: Michael J. Howard, Scottsdale, Ariz.; Thomas V. White, Placerville, Calif.; Anthony K. Hedley, Paradise Valley, Ariz.; Oliver S. Mills, Sacramento, Calif.

[73] Assignee: Synvasive Technology, Inc., Sacramento, Calif.

[21] Appl. No.: 967,268

[22] Filed: Nov. 7, 1997

Related U.S. Application Data

[63] Continuation of Ser. No. 510,793, Aug. 3, 1995, abandoned.

[51] Int. Cl.⁶ .................................................. A61B 17/15
[52] U.S. Cl. ............................... 606/87; 606/88; 606/82
[58] Field of Search ............................... 606/79, 82, 86, 606/87, 88, 89

[56] References Cited

U.S. PATENT DOCUMENTS

| | | |
|---|---|---|
| 2,323,319 | 7/1943 | Finnell ........................................ 83/761 |
| 3,651,541 | 3/1972 | Jaccard . |
| 3,667,330 | 6/1972 | Kobernick . |
| 3,910,146 | 10/1975 | Earl . |
| 4,179,810 | 12/1979 | Kirsch . |
| 4,313,543 | 2/1982 | Paterson ................................. 209/212 |
| 4,325,287 | 4/1982 | Beerens ..................................... 83/745 |
| 4,501,268 | 2/1985 | Comparetto . |
| 4,524,766 | 6/1985 | Petersen . |
| 4,535,654 | 8/1985 | White . |
| 4,627,194 | 12/1986 | Friel . |
| 4,627,425 | 12/1986 | Reese . |
| 4,658,875 | 4/1987 | Grabovac . |
| 4,718,413 | 1/1988 | Johnson . |
| 4,736,737 | 4/1988 | Fargie et al. . |
| 4,757,810 | 7/1988 | Reese . |
| 4,759,350 | 7/1988 | Dunn et al. . |
| 4,841,975 | 6/1989 | Woolson . |
| 4,892,093 | 1/1990 | Zarnowski et al. . |
| 4,926,847 | 5/1990 | Luckman . |
| 4,952,214 | 8/1990 | Comparetto . |
| 5,021,056 | 6/1991 | Hofmann et al. . |
| 5,042,983 | 8/1991 | Rayhack . |
| 5,050,276 | 9/1991 | Pemberton ............................... 24/303 |
| 5,092,869 | 3/1992 | Waldron . |
| 5,129,909 | 7/1992 | Sutherland . |
| 5,147,364 | 9/1992 | Comparetto . |
| 5,234,432 | 8/1993 | Brown . |
| 5,250,050 | 10/1993 | Poggie et al. . |
| 5,275,603 | 1/1994 | Ferrante et al. . |
| 5,306,276 | 4/1994 | Johnson et al. . |
| 5,350,382 | 9/1994 | Armstrong . |
| 5,364,401 | 11/1994 | Ferrante et al. . |
| 5,405,349 | 4/1995 | Burkinshaw et al. . |
| 5,413,579 | 5/1995 | Tom Du Toit . |

FOREIGN PATENT DOCUMENTS 1609472A  1/1988  U.S.S.R. .

*Primary Examiner*—Michael Powell Buiz
*Assistant Examiner*—David O. Reip
*Attorney, Agent, or Firm*—Daniel J. Meaney, Jr.

[57] ABSTRACT

A surgical saw blade guide or milling instrument guide comprising a guide body having a guiding surface thereon, and containing a magnet therein which exerts attractive force in a direction toward the guide body for attracting a bone saw blade or milling instrument to the guiding surface. The surgical saw blade guide or milling instrument guide can comprise a plurality of magnets and the magnet or magnets can themselves form part of the guiding surface. Also, a method of cutting a bone comprising the steps of magnetically attracting a surgical bone saw blade or milling instrument to a surgical saw blade guide or milling instrument guide containing a magnet, actuating a bone saw coupled to the bone saw blade or actuating a milling instrument, advancing the bone saw blade or milling instrument into the bone thereby cutting the bone, and detaching the saw blade or milling instrument from the guide.

26 Claims, 3 Drawing Sheets

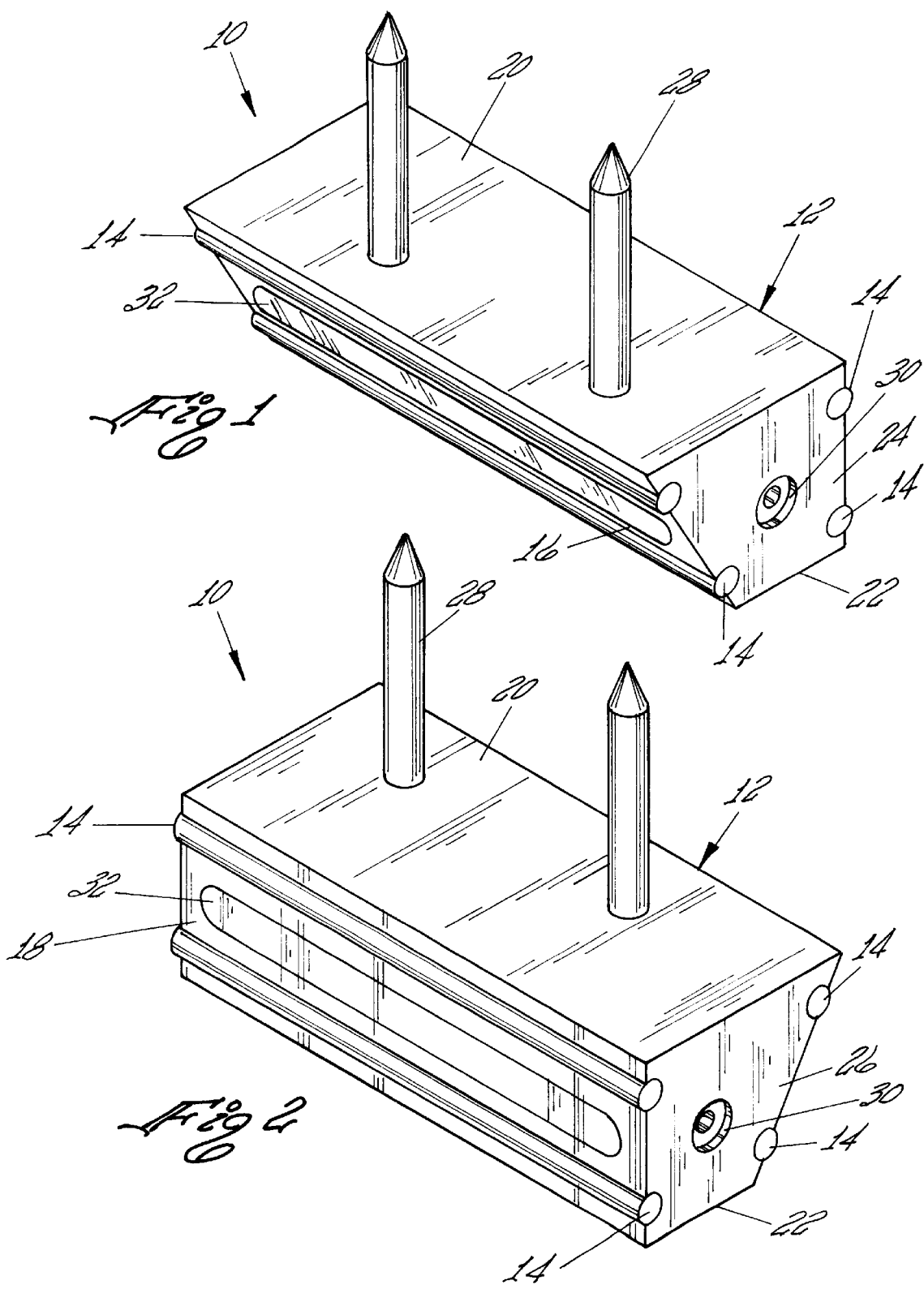

BONE SAW BLADE GUIDE WITH MAGNET

This application is a continuation of application Ser. No. 08/510,793, filed Aug. 3, 1995, now abandoned.

BACKGROUND

In many types of surgical procedures, surgeons must cut bone precisely with bone saws or milling instruments. Surgical bone saws and milling instruments are generally known in the surgical field as surgical instruments. For example, when a surgeon implants a prosthetic knee, the surgeon must cut or mill the distal femur to within a few thousandths of an inch of the desired planes for a prosthetic knee to fit properly. If the bone is not shaped accurately, the prosthetic implant can become loose over time or can function poorly causing a gait disturbance or chronic pain. In either case, surgery may be necessary to revise or replace the prosthetic knee. These surgical revisions are costly and associated with significant morbidity.

In order to shape bone precisely, bone saw blade guides and milling instrument guides, generally known in the surgical field as surgical cutting guides, have been developed to direct the bone saw blade or bone mill into the bone. There are two general types of bone saw blade guides. First, some guides have an open-faced guiding surface which the bone saw blade contacts while cutting bone. Second, some bone saw blade guides have a slot, into which the bone saw blade is guided between opposing sides of the slot while cutting bone.

Each type of bone saw blade guide has advantages and disadvantages. Guides with an open-faced guiding surface advantageously allow the surgeon excellent visibility of the bone cut while the bone saw blade is cutting. After making the cut, the surgeon is able to determine whether the cut is flat and accurate without removing the guide from the bone. Further, guides with an open-faced guiding-surface advantageously do not tend to cause bone saw blades to bind as a result of pivoting action at the edges of the guides.

Bone saw blade guides with an open-faced surface, however, disadvantageously require the surgeon to maintain excessive pressure on the bone saw blade perpendicular to the open-faced guiding surface during cutting in order to keep the bone saw blade in contact with the open-faced guiding surface. If the surgeon fails to maintain adequate pressure, the bone saw blade can move out of the desired cutting path causing an inaccurate cut.

Slotted bone saw blade guides, on the other hand, capture the bone saw blade between two opposing surfaces. This capture advantageously avoids the need for a surgeon to maintain excessive pressure on a single open-faced guiding surface during cutting in order to keep the bone saw blade aligned with the guiding surface.

The slot in slotted bone saw blades must be slightly wider than the thickness of the bone saw blade to permit entry of blades with set teeth. Therefore, the bone saw blade can disadvantageously pivot on the edges of the slot thereby reducing the accuracy of the cut, and a surgeon must maintain pressure on the bone saw blade to counteract such movements. Further, bone saw blades tend to bind in the slotted guide when they pivot on the edge of the slot. Friction between the bone saw blade and the slot can cause material from the slotted guides, such as stainless steel debris, to enter the surgery site.

Also disadvantageously, bone saw blade guides with slots tend to obstruct the surgeon's view of the bone cut, making it difficult for the surgeon to determine whether the cut is flat and accurate without removing the guide from the bone. Also, slotted guide are heavier, and therefore more difficult to work with, than guides with an open-faced guiding surface, and slotted guides are more expensive than guides with an open-faced guiding surface.

Milling instrument guides have some of the same disadvantages as bone saw blade guides. For example, milling instruments guides can obstruct the view of bone being milled. Further, milling instrument guides can require the surgeon to maintain excessive pressure on the bone mill during milling in order to keep the milling instrument in contact with the guiding surface of the milling instrument guide.

Thus, there remains a need for a surgical bone saw blade guide or milling instrument guide and a method of cutting or milling bone which allows the surgeon to make an accurate bone cut without having to maintain excessive pressure on the bone saw blade or bone mill to keep the bone saw blade or bone mill properly aligned and, at the same time, allows the surgeon good visualization of the forming bone cut to determine that the cut is accurate and to determine that the cut is flat and accurate without removing the guide from the bone after the cut has been completed. It would, therefore, be advantageous to have a bone saw blade guide or milling instrument guide and a method of cutting or milling bone having these features.

SUMMARY

The present invention is directed to a bone saw blade guide or milling instrument guide and a method of cutting bone. In one embodiment, the invention is a surgical saw blade guide or milling instrument guide comprising a guide body having a guiding surface thereon. The guide body contains a magnet which exerts attractive force in a direction toward the guide body for attracting a bone saw blade or milling instrument to the guiding surface. The magnet can be completely embedded in the guide body and can be covered by a cover which forms part of a surface of the bone saw blade guide or milling instrument guide.

In one embodiment, the magnet can be a plurality of magnets. The plurality of magnets can be removable and can be interchangeable. In a preferred embodiment, the magnet exerts attractive force in a direction substantially normal to the guiding surface.

The surgical saw blade guide or milling instrument guide of the present invention can be configured to cut a femur or a tibia for implanting a unit of a prosthetic knee.

The present invention also includes a method of cutting a bone comprising the steps of, first, magnetically attracting a surgical bone saw blade or milling instrument to a surgical saw blade guide or milling instrument guide, respectively, containing a magnet. The magnet exerts an attractive force in a direction towards the guide. Next, the bone saw blade or bone mill is advanced into the bone, thereby cutting the bone. Then, the saw blade or milling instrument is detached from the guide. The method can comprise the additional step of actuating a bone saw coupled to the bone saw blade or actuating the milling instrument before or after magnetically attracting the surgical bone saw blade or milling instrument, respectively, to the guide. This method is suitable for use on the scapula, humerus, ulna, radius, pelvis, femur, patella, tibia, fibula, talus and calcaneus, among other bones.

Also provided by the present invention is a method of cutting a bone comprising the steps of, first, reversibly attaching a surgical saw blade guide or milling instrument guide to the bone. The guide comprises a guide body having a guiding surface thereon. The guide body contains a magnet which exerts attractive force in a direction toward the guiding surface for attracting a bone saw blade or milling instrument to the guiding surface. Next, a bone saw blade attached to a bone saw, or a milling instrument is placed against the guiding surface such that the saw blade or milling instrument is attracted to the guiding surface by the magnet. Then, the bone saw blade or bone mill is advanced into the bone, thereby cutting the bone. Further, the bone saw blade or milling instrument is removed from the saw blade guiding surface. The method can comprise the additional step of actuating a bone saw coupled to the bone saw blade, or actuating the milling instrument before or after magnetically attaching the surgical bone saw blade to the surgical saw blade guide. This method is suitable for use on the scapula, humerus, ulna, radius, pelvis, femur, tibia, patella, fibula, talus and calcaneus, among other bones.

FIGURES

These features, aspects and advantages of the present invention will become better understood with regard to the following description and appended claims in the accompanying figures where:

FIG. 1 is an anterior-right lateral perspective view of a surgical bone saw blade guide according to one aspect of the present invention;

FIG. 2 is a posterior-left lateral perspective view of the surgical bone saw blade guide shown in FIG. 1;

Figure 6:
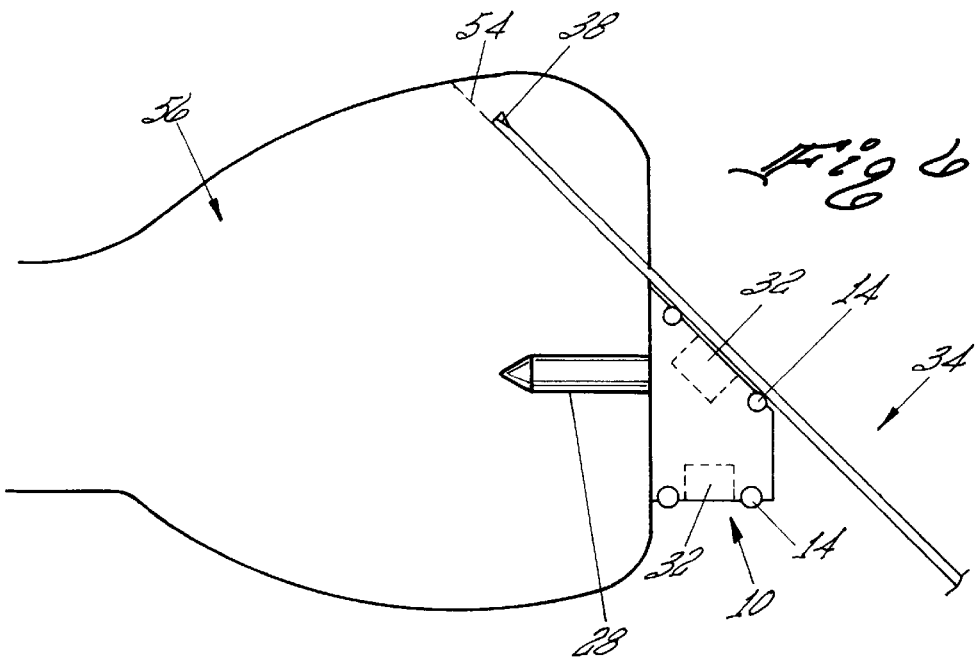
FIG. 6 is an environmental view of a surgical bone saw blade guide as shown in FIGS. 1 and 2, showing the anterior chamfer cut in the distal femur being made.
Figure 7:
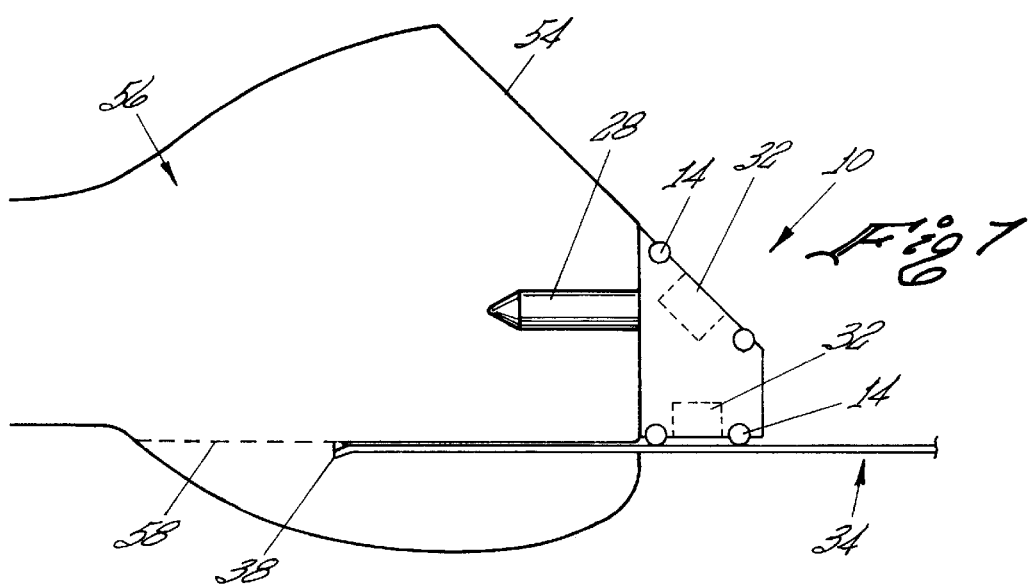
Figure 8:
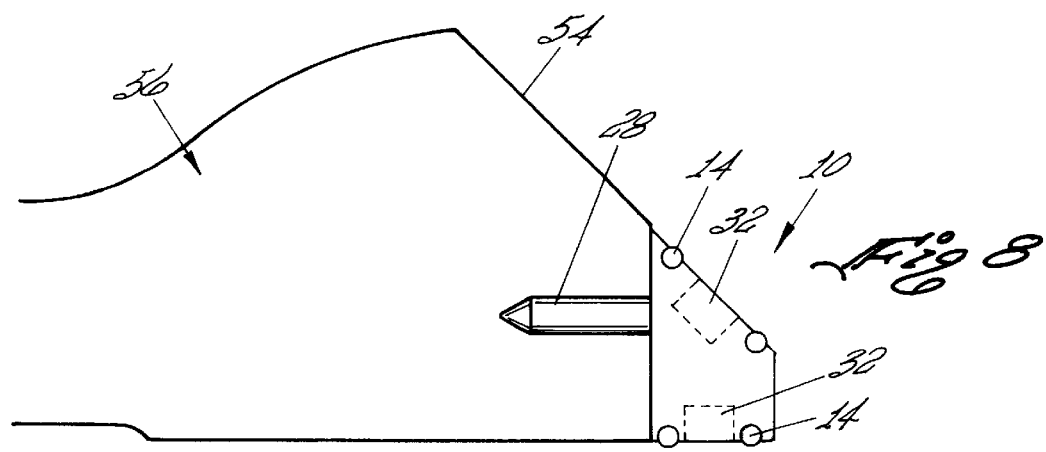

FIG. 7 is an environmental view of a surgical bone saw blade guide as shown in FIGS. 1 and 2, showing the posterior bone cut in the distal femur being made; and FIG. 8 is an environmental view of a surgical bone saw blade guide as shown in FIGS. 1 and 2, showing the position of the guide shown in FIGS. 6 and 7 after the posterior bone cut.

DESCRIPTION

According to one embodiment of the present invention, there is provided a surgical bone saw blade guide or milling instrument guide having a body and at least one guiding surface, and incorporating a magnet. The magnet exerts an attractive force in a direction towards the guide body for attracting a bone saw blade or milling instrument to the guiding surface. In use, a surgical bone saw blade or milling instrument which is subject to magnetic attraction, such as a martensitic or ferritic stainless steel bone saw blade or milling instrument, is placed against the guiding surface such that the magnet assists in keeping the bone saw blade or milling instrument aligned against the guiding surface while the bone saw blade or bone mill is cutting a bone having a bone portion to be cut. Magnetic attraction of the bone saw blade or milling instrument in contact with the guiding surface promotes an accurate bone cut. Further, the surgeon can better concentrate on making the cut rather than keeping the bone saw blade or milling instrument in contact with the guiding surface.

Surgical bone saw blade guides and milling instrument guides of the present invention are particularly suited for making the necessary cuts in the tibia and femur during prosthetic knee implantation surgery. However, surgical bone saw blade guides and milling instrument guides according to the present invention can also be used for cutting or milling bone in other types of surgeries, including arthroplasties involving the shoulder, elbow, wrist, hip and ankle, as well as other surgeries which require accurate cuts in bone. Examples of bones which can be accurately cut by using surgical bone saw blade guides and milling instrument guides of the present invention include the scapula, humerus, ulna, radius, pelvis, femur, tibia, fibula, patella, talus and calcaneus.

According to one embodiment of the present invention, there is provided a surgical bone saw blade guide comprising a surgical bone saw blade guide body. The body has at least one separate blade guiding surface thereon. The exact shape of the guide body and position and number of the blade guiding surfaces depends upon which bone cut or bone cuts are going to be made using the blade guide, as would be understood by those with skill in the art with reference to the disclosure herein.

Referring now to FIGS. 1 and 2, there are illustrated an anterior-right lateral perspective view and a posterior-left lateral perspective view, respectively, of a surgical bone saw blade guide 10 having features of the present invention. The surgical bone saw blade guide 10 illustrated in FIGS. 1 and 2 is of a configuration useful for making the anterior chamfer femoral and posterior femoral bone cuts during prosthetic knee implantation surgery, after the distal femoral cut has been made.

The surgical bone saw blade guide 10 according to the present invention shown in FIGS. 1 and 2 comprises a surgical bone saw blade guide body 12 which has at least one blade guiding surface 14 thereon, an anterior surface 16, a posterior surface 18, a superior surface 20, an inferior surface 22, a right lateral surface 24 and a left lateral surface 26. The overall shape of the body for surgical bone saw blade guides according to the present invention will depend upon the bone cut or bone cuts which the guide is to assist in making. For example, the body 12 shown in FIGS. 1 and 2 has a generally trapezoidal shape when viewed from either the right lateral surface 24 or from the left lateral surface 26. The body can, however, have other shapes as would be understood by those with skill in the art with reference to the disclosure herein, depending on the bone cut or bone cuts to be made.

The body 12 can comprise any of a variety of materials, such as coated steel, stainless steel, aluminum, plastic, titanium, cobalt-chrome or ceramic, which have the necessary abrasion resistance and hardness as would be known to those with skill in the art. In one preferred embodiment, the body 12 comprises stainless steel. In another preferred embodiment, the body 12 comprises aluminum.

The surgical bone saw blade guide 10 further comprises at least one blade guiding surface 14 on the body 12. In a preferred embodiment, the blade guiding surface can be coincident with one of the surfaces of the body such as the anterior surface, the posterior surface, the superior surface, the inferior surface, the right lateral surface, the left lateral surface or another surface of the body. The preferred embodiment shown in FIGS. 1 and 2, has a plurality of the blade guiding surfaces 14, each configured as two longitudinal rails of material having a circular cross-section and attached to the surface of the blade guide body 12 and configured to separate a bone saw blade from the rest of the blade guide body 12. As can be seen in FIGS. 1 and 2, both the anterior surface 16 and the posterior surface 18 of the body 12 have two blade guiding surfaces 14 thereon, each of which are embedded in the anterior surface 16 and posterior surface 18 and each of which extend externally to the respective surfaces.

The blade guiding surfaces 14 can comprise material identical with the body or can comprise material substantially different. The blade guiding surfaces 14 can, for example, comprise ceramic, stainless steel, titanium or aluminum as would be understood by those with skill in the art. In a preferred embodiment, the blade guiding surfaces 14 comprise ceramic.

In a preferred embodiment, the surgical bone saw blade guide according to the present invention comprises at least one bone connector. The embodiment 10 of the present invention shown in FIGS. 1 and 2 further comprises two bone connectors 28. The bone connectors 28 are coupled to the surgical bone saw blade guide 10 for reversibly attaching the body 12 to bone. The bone connectors 28 preferably comprise biocompatible material having properties suitable for reversibly anchoring the surgical bone saw blade guide body 12 into the bone to be cut. In a preferred embodiment, the bone connectors 28 comprise stainless steel or ceramic.

In a preferred embodiment 10 shown in FIGS. 1 and 2, the connectors 28 are smooth pins. These pins 28 can be integrally attached to the body 12 or can be detachably connected to the body 12. Other types of bone connectors are suitable for use with the surgical bone saw blade guide of the present invention. Such connectors include bone screws, rods and bone clamps as would be understood by those with skill in the art with reference to the disclosure herein.

The body 12 preferably includes at least one mechanism for attaching a handle (not shown) in either the right lateral surface 24 or left lateral surface 26, or a plurality of mechanisms for attaching a handle in both the right lateral surface 24 and the left lateral surface 26. The embodiment 10 shown in FIGS. 1 and 2 comprises two such mechanisms, each mechanism comprising a bore hole 30 extending into the body 12 from the right lateral surface 24 and another bore hole 30 extending into the body 12 from the left lateral surface 26, each bore hole 30 substantially parallel with the posterior surface 18 and approaching the superior surface 20 of the body 12 centrally. Each bore hole 30 preferably includes an internally threaded surface through at least part of the interior of the hole. A corresponding externally threaded surface on one end of the handle (not shown) is used to reversibly attach a handle to at least one side of the body 12. The handle allows the surgeon to manipulate the guide 10 more easily to position it on the bone and to remove the guide from the bone after the cut is completed.

The surgical bone saw blade guide 10 according to the present invention comprises at least one magnet 32 having a dimension at least equal to the known width of the surgical instrument to be used therewith. The magnet 32 exerts attractive force in a direction toward the blade guide body 12 for attracting a bone saw blade to the blade guiding surface 14. In a preferred embodiment, the magnet exerts attractive force in a direction substantially normal to the blade guiding surface.

The magnet 32 can be any of a variety of suitable materials as is known to those with skill in the art such as alnicos, ceramics and rare earths. For example, in a preferred embodiment, the magnet 32 is a rare earth such as samarium-cobalt and neodymium-iron-boron because of their high energy product relative to other magnetic materials.

The strength of the magnet should be large enough to significantly attract the saw blade to the guide while still allowing movement of the blade by the surgeon. In a preferred embodiment, the magnet 32 comprises material having a Maximum energy Product (BHmax) of between about 0.5 Megagauss Oersteds and about 45 Megagauss Oersteds (MGO). In another preferred embodiment, the magnet 32 comprises material having a Maximum energy Product (BHmax) of between about 18 Megagauss Oersteds and about 32 Megagauss Oersteds (MGO). The magnetic flux exerted by the magnet 32 can be positive or negative, but in either case, must attract the saw blade to the body.

The blade guiding surface can itself comprise a magnet. However, in a preferred embodiment, the magnet is embedded in the surgical bone saw blade guide body such that a bone saw blade resting on one or more blade guiding surfaces would not directly contact the magnet. The magnet can be placed in a depression in the blade guide body having a shape suitable to hold the magnet. Alternately, a slot can be formed within the blade guide body which permits placement of the magnet through a lateral blade guide surface.

The magnet 32 can be removable so that other magnets can be placed in the body 12. This allows replacement of a damaged magnet with a new magnet or replacement of a magnet having one attractive force with a magnet having a different attractive force.

Figure 3:
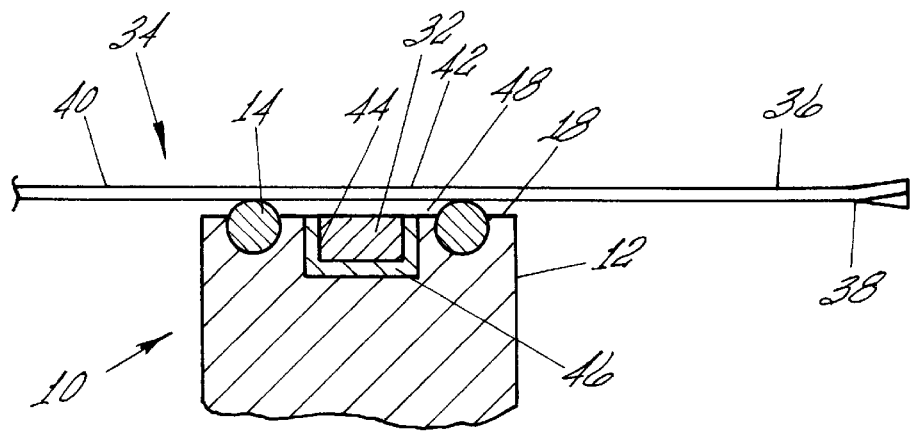
FIG. 3 is partial sagittal cross-sectional view of the guide body through the posterior surface of the surgical bone saw blade guide shown in FIGS. 1 and 2.

Referring now to FIG. 3, there is illustrated a partial sagittal cross-sectional view through the posterior surface 18 of the surgical bone saw blade guide body 12 shown in FIGS. 1 and 2 showing the magnet 32 embedded in the body. A surgical bone saw blade 34 having a distal end 36 with teeth 38 and a proximal end 40 coupled to a bone saw, not shown, is illustrated to show the relationship between the shaft 42 of the bone saw blade 34, the blade guiding surfaces 14 and the magnet 32 when the surgical bone saw blade 34 is cutting bone.

As can be seen in FIG. 3, the magnet 32 is embedded in the blade saw guide body 12. The exterior-most surface 44 of the magnet 32 forms part of the posterior surface 18 of the body 12. While the magnet 32 is shown as rectangular in cross-section, the magnet 32 could be round, oval, or any other suitable shape as would be understood by those with skill in the art. Preferably, the magnet is isolated from the body by material 46, such as silicone or epoxy, as shown in FIG. 3, which also serves to retain the magnet within the body 12.

As can be seen in FIG. 3, when there are multiple blade guiding surfaces 14 on the body 12, a small gap 48 is created between the shaft 42 of the bone saw blade 34 and the body 12, itself. Therefore, in the embodiment 10 shown in FIG. 3, the blade saw shaft 42 is separated from the magnet 32 by the gap 48.

Figure 4:
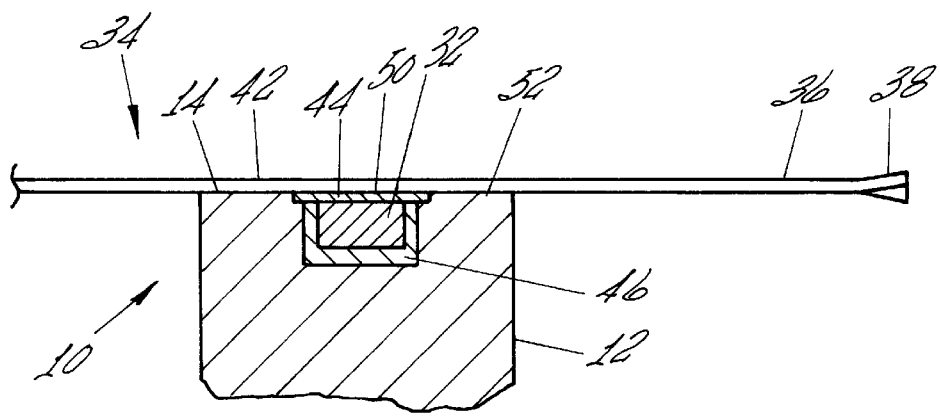
FIGS. 4 and 5 are partial sagittal cross-sectional views through the blade guiding surface of surgical bone saw blade guide bodies according to two preferred embodiments of the present invention.
Figure 5:
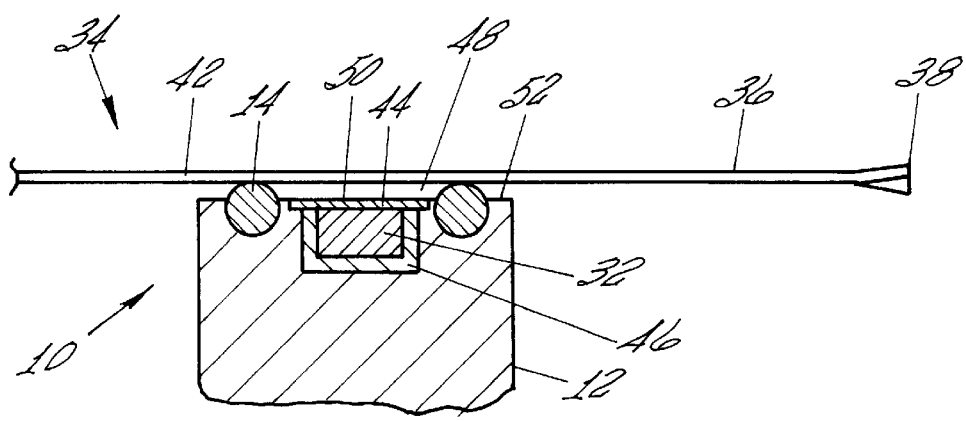

Referring now to FIGS. 4 and 5, there are illustrated partial sagittal cross-sectional views through the blade guiding surfaces 14 of surgical bone saw blade guide bodies 12 according to two preferred embodiments 10 of the present invention. In both embodiments 10, the exterior-most surface 44 of the magnet 32 is covered by magnet cover 50. Magnet cover 50 forms part of the surface 52 of the body 12 and permits magnetic flux to pass through, thereby acting on the bone saw blade 34. The magnet cover 50 prevents contact of the magnet 32 by a bone saw blade which can damage the magnet 32. The cover 50 also protects the magnet 32 from contact with moisture and sterilization fluids, among others substances present in the surgical field.

The magnet cover 50 can comprise any of a variety of suitable material as would be appreciated by those with skill in the art with reference to the disclosure herein. For example, in a preferred embodiment the cover comprises stainless or coated steel because these materials protect the magnet 32 from bone saw blade contact while minimally reducing the magnetic flux exerted by the magnet 32 on the bone saw blade. The cover can also comprise aluminum or plastic, such as polyetherimde (for example, Ultem®), polyethylene, polysulfone, polyimide (for example, Vespel®), phenolics (for example, Baklite®). The cover can be attached by an adhesive or by mechanical means, such as welding, fasteners or pins among other means, as would be understood by those with skill in the art.

In FIG. 4, the surface 52 of the surgical bone saw blade guide 10, along with the magnet cover 50, themselves comprise the blade guiding surfaces 14. In this embodiment, a bone saw blade 34 rests directly on the surface 52 and magnet cover 50 while cutting bone.

In FIG. 5, the surgical bone saw blade guide 10 comprises two blade guiding surfaces 14 configured as two longitudinal rails of material attached to the surface 44 of the blade guide body and configured to separate a bone saw blade 34 from the rest of the blade guide body 12. Therefore, in FIG. 5, the bone saw blade is separated from the magnet 32 by both the magnet cover 50 and a gap 48.

According to another embodiment of the present invention, not shown, the surgical bone saw blade guiding surfaces can be integral with the body and can comprise material substantially the same as most of the remainder of the body. In this embodiment, the guiding surfaces are raised extremities above the body surface, rather than incorporated guiding surfaces of material dissimilar to the remainder of the body.

Using magnets incorporated into guides, the manner disclosed herein advantageously allows the use of thinner and lighter bone saw blades. Such blades generate less heat while cutting, are easier to manipulate and increase the amount of power imparted to the blade by a surgical saw. Further, using a guide with a magnet according to the present invention allows a surgeon to maintain tactile sensation of the relation of the blade to the guide because of the magnetic attraction, even when the surgeon angles the surgical saw coupled to the saw blade.

According to another embodiment of the present invention, there is provided a slotted surgical bone saw blade guide having a magnet therein configured to attract a bone saw blade to one side of the slot. Among other advantages disclosed herein, this attraction assists in reducing unwanted movements of the blade. Magnets incorporated in slotted guides, according to the present invention, also reduce the chance that debris from the slotted guides, such as stainless steel, will enter the surgical site by attracting such debris to the guide body.

According to another embodiment of the present invention, there is provided a bone milling instrument guide incorporating a magnet to assist in directing the bone mill while the bone mill is cutting bone. The bone milling instrument guide has structures and embodiments equivalent to those described above for surgical bone saw blade guides, as would be understood by those with skill in the art with reference to the disclosure herein.

Guides with magnets according to the present invention advantageously improve the accuracy of the bone cut. This increase in accuracy is due in part to improved ability to create an initial cut in the bone of a desired width and direction.

According to another embodiment of the present invention, there is provided a method of cutting bone. The method comprises first, magnetically attracting a surgical bone saw blade or milling instrument to a surgical saw blade guide or milling instrument guide, respectively, which contains a magnet. The magnet exerts attractive force in a direction toward the guide such that the saw blade or milling instrument is attracted to the guide. Next, the bone saw blade or milling instrument is advanced into the bone thereby cutting the bone. During this procedure, the saw blade or milling instrument is held against the guide partly, at least, by attractive force from the magnet. After the bone is cut, the saw blade or milling instrument is detached from the guide. A bone saw coupled to the bone saw blade, or the milling instrument can be actuated before or after the bone saw blade or milling instrument is attracted to the guide, depending on the preference of the surgeon. This method is suitable for cutting a variety of bones, such as the scapula, humerus, ulna, radius, pelvis, femur, tibia, fibula talus and calcaneus.

According to another embodiment of the present invention, there is provided a method of cutting bone comprising the steps of first, attaching a surgical saw blade guide or a milling instrument guide to the bone to be cut. The guide comprises a guide body which has a blade guiding surface or milling instrument guiding surface, respectively, thereon. The guide body contains a magnet which exerts attractive force in a direction toward the guiding surface for attracting a bone saw blade or milling instrument to the guiding surface. The bone saw blade or milling instrument is then placed against the guiding surface such that the saw blade or milling instrument is attracted to the guiding surface by the magnet within the guide body. Next, the bone saw blade or bone mill is advanced into the bone thereby cutting the bone. Finally, the bone saw blade or milling instrument is removed from the guiding surface. This method is also suitable for cutting a variety of bones, such as, the scapula, humerus, ulna radius, pelvis, femur, tibia, fibula talus and calcaneus.

Referring now to FIGS. 6 through 8, there are illustrated environmental views of a surgical bone saw blade guide 10 as shown in FIGS. 1 and 2, after the distal femoral cut has been made, showing an anterior chamfer cut 54 in a distal femur 56 being made (FIG. 6), a posterior cut 58 in the distal femur 56 being made (FIG. 7) and the position of the guide 10 after the posterior cut 58 is made (FIG. 8), respectively. As can be seen, the bone saw blade rests on the blade guiding surfaces 14 but is separated from the magnet 32 by a gap 48. Further, the guide 10 does not obstruct the surgeon's view of the bone cut as would a slotted guide.

Although the present invention has been described in considerable detail with reference to certain preferred embodiments thereof, other embodiments are possible. For example, the present invention also includes a kit comprising the surgical saw blade guide with a magnet according to the present invention and a plurality of magnets, wherein each magnet is configured to removably fit within the blade guide body. Further, a surgical saw blade guide having a slot or slots for one or more cuts and an open-faced guiding surface with a magnet for one or more cuts is contemplated within the scope of the present invention. Therefore, the spirit and scope of the appended claims should not be limited to the description of the preferred embodiments contained herein.

We claim:

1. A surgical cutting guide for use with a surgical instrument having a known width and formed of magnetic material comprising
    a guide body having a connector on one surface thereof for detachably connecting the guide body to a bone having a bone portion to be cut, said guide body further including a separate guiding surface having a length which is at least substantially equal in length to the bone portion to be cut and a magnet forming part of said separate guiding surface having a dimension at least equal to the known width and positioned to be substantially in alignment with the bone portion to be cut and to magnetically attract and exert an attractive force on the surgical instrument in a direction towards the guide body for attracting the surgical instrument to and slideably against the guiding surface.

2. The surgical cutting guide of claim 1, wherein the guide body comprises coated steel, stainless steel, aluminum, plastic, titanium or cobalt-chrome.

3. The surgical cutting guide of claim 1, wherein the magnet is selected from the group consisting of alnicos, ceramics and rare earths.

4. The surgical cutting guide of claim 1, wherein the magnet is selected from the group consisting of samarium-cobalt and neodymium-iron-boron.

5. The surgical cutting guide of claim 1, wherein the magnet comprises material having a Maximum energy Product (BHmax) of between about 0.5 Megagauss Oersteds and about 45 Megagauss Oersteds (MGO).

6. The surgical cutting guide of claim 1, wherein the magnet is completely embedded in the guide body and is enclosed by a cover formed of a material which minimally reduces magnetic flux exerted by the magnet on the surgical instrument.

7. The surgical cutting guide of claim 1, wherein the magnet is a plurality of magnets.

8. The surgical cutting guide of claim 1, wherein the magnet exerts the attractive force in a direction substantially normal to the blade guiding surface.

9. The surgical cutting guide of claim 1, wherein the magnet is removable from the guide body.

10. The surgical cutting guide of claim 1, wherein the guide body further comprises a magnet cover.

11. The surgical cutting guide of claim 10, wherein the cover is selected from the group consisting of coated steel, stainless steel, aluminum and plastic.

12. The surgical cutting guide of claim 1, wherein said connector comprises at least one bone connector coupled to the guide body for reversibly attaching the guide body to said bone having a bone portion to be cut.

13. The surgical cutting guide of claim 12, wherein the at least one bone connector is a bone pin.

14. The surgical cutting guide of claim 1, wherein the separate guiding surface is selected from the group consisting of coated steel, stainless steel, titanium, aluminum and plastic.

15. The surgical cutting guide of claim 1, wherein the guide body is configured to cut a femur for implanting a unit of a prosthetic knee.

16. The surgical cutting guide of claim 1, wherein the guide body is configured to cut a tibia for implanting a unit of a prosthetic knee.

17. A surgical saw blade guide kit comprising the surgical cutting guide of claim 1 and a plurality of magnets, wherein each magnet is configured to removably fit within the guide body.

18. A surgical cutting guide for use with a surgical instrument having a known width and formed of a magnetic material comprising a guide body having a separate guiding surface thereon having a length which is at least substantially equal in length to a bone portion of a bone to be cut, said guide body further having at least one bone connector coupled to the guide body on a surface other than the guiding surface for reversibly attaching the guide body to said bone having a bone portion to be cut, said guide body containing in the guiding surface a magnet having a dimension at least equal to the known width and substantially in alignment with the bone portion to be cut and wherein said magnet exerts an attractive force in a direction towards the guide body for attracting the surgical instrument to and slideably against the guiding surface.

19. A method of cutting a bone comprising the steps of
    a) detachably connecting with a connector a surgical cutting guide to a bone having a bone portion to be cut wherein the surgical cutting guide comprises a guide body having a separate guiding surface having a length which is at least substantially equal in length to the bone portion to be cut;
    b) magnetically attracting a surgical instrument having a known width and formed of a magnetic material to the surgical guide wherein the guiding surface contains a magnet therein having a dimension at least equal to the known width and positioned to be in alignment with the bone portion to be cut, the magnet exerting an attractive force on the surgical instrument in a direction towards the guide body and slideably against the guiding surface;
    c) advancing the surgical instrument into the bone having a portion to be cut, thereby cutting the bone portion to be cut; and
    d) removing the surgical instrument from the guiding surface.

20. The method of claim 19, comprising the additional step of
    detaching the surgical cutting guide from the bone having a portion to be cut upon completion of cutting thereof.

21. The method of claim 19, wherein the step of detachably connecting the connector to a bone having a portion to be cut includes a bone which is selected from the group consisting of the scapula, humerus, ulna, radius, pelvis, femur, tibia, fibula, patella, talus and calcaneus.

22. A method of cutting a bone comprising the steps of:
    a) reversibly attaching with a connector a surgical cutting guide to the bone having a portion to be cut, wherein the surgical cutting guide comprises a guide body having a separate guiding surface thereon having a length which is at least substantially equal in length said bone having a portion to be cut and wherein the connector is used for reversibly attaching the guide body to the bone having a portion to be cut, the guide body containing a magnet which exerts an attractive force on a surgical instrument having formed of a magnetic material and wherein said magnet has a dimension at least equal to the known width and positioned to be in alignment with the bone portion to be cut, said magnet exerting said attractive force in a direction towards the guiding surface for attracting the surgical instrument to and slideably against the guiding surface;
    b) placing the surgical instrument against the guiding surface such that the surgical instrument is attracted to the guiding surface by the magnet;

c) advancing the surgical instrument into the bone portion to be cut, thereby cutting the bone; and d) removing the surgical instrument from the guiding surface.

23. The method of claim 22, comprising the additional step of actuating a bone saw coupled to the surgical instrument before step b).

24. The method of claim 22, wherein the step of reversibly connecting to a bone includes a bone which is selected from the group consisting of the scapula, humerus, ulna, radius, pelvis, femur, tibia, fibula, patella, talus and calcaneus.

25. A method of cutting a bone comprising the steps of:

a) providing the surgical cutting guide of claim 1;

b) reversibly attaching with a connector the surgical cutting guide to the bone having a portion to be cut;

c) placing the surgical instrument having a magnetic material against the guide surface such that the surgical instrument is attracted to and slideably against the guiding surface by the magnet;

d) advancing the surgical instrument into the bone, thereby cutting the portion of the bone to be cut; and e) removing the surgical instrument from the guiding surface.

26. The method of claim 25, wherein the step of reversibly attaching to a bone having a portion to be cut includes a bone which is selected from the group consisting of the scapula, humerus, ulna, radius, pelvis, femur, tibia, fibula, patella, talus and calcaneus.

* * * * *